(12) United States Patent
Zhao

(10) Patent No.: US 12,366,307 B2
(45) Date of Patent: Jul. 22, 2025

(54) PISTON MECHANISM, FLUID CONTROL MECHANISM AND APPLICATION THEREOF

(71) Applicant: EVERLAST HEALTHCARE LIMITED, Hong Kong (CN)

(72) Inventor: Haifeng Zhao, Hong Kong (CN)

(73) Assignee: EVERLAST HEALTHCARE LIMITED, Hong Kong (CN)

( * ) Notice: Subject to any disclaimer, the term of this patent is extended or adjusted under 35 U.S.C. 154(b) by 111 days.

(21) Appl. No.: 18/270,026

(22) PCT Filed: Dec. 30, 2021

(86) PCT No.: PCT/CN2021/143088
§ 371 (c)(1),
(2) Date: Jun. 28, 2023

(87) PCT Pub. No.: WO2022/143900
PCT Pub. Date: Jul. 7, 2022

(65) Prior Publication Data
US 2024/0060576 A1    Feb. 22, 2024

(30) Foreign Application Priority Data
Dec. 31, 2020  (CN) .......................... 202011639849.5

(51) Int. Cl.
*F16K 99/00*  (2006.01)
*B01L 3/00*  (2006.01)

(52) U.S. Cl.
CPC .... *F16K 99/0011* (2013.01); *B01L 3/502738* (2013.01); *F16K 99/0005* (2013.01); *F16K 99/0042* (2013.01); *B01L 2400/0478* (2013.01)

(58) Field of Classification Search
None
See application file for complete search history.

(56) References Cited

U.S. PATENT DOCUMENTS 4,364,543 A * 12/1982  Soya ...................... F16K 31/50
                                                  137/315.27
5,851,003 A * 12/1998  Aoki ...................... F16K 31/04
                                                      251/264

(Continued)

FOREIGN PATENT DOCUMENTS

CN  101384846 A  3/2009
CN  102679039 A  9/2012

(Continued)

OTHER PUBLICATIONS

International Search Report from PCT Application No. PCT/CN2021/143088, Mar. 30, 2022.

(Continued)

*Primary Examiner* — Matthew W Jellett
(74) *Attorney, Agent, or Firm* — Workman Nydegger

(57) ABSTRACT

A fluid control mechanism includes a chamber, a chamber wall, a piston provided within the chamber, and at least one fluid channel. A bottom portion of the chamber is configured to be in communication with the fluid channel. An opening connecting the fluid channel and the chamber is arranged at the bottom portion of the chamber. A piston mechanism has a chamber and a chamber wall, and a piston and a piston motion control member provided within the chamber. The piston motion control member is provided with external threads forming a screw thread pair with internal threads on the chamber wall, and is configured to rotate along the threads to move within the chamber for driving the piston to move in the chamber. The piston mechanism and the fluid control device can accurately control liquid in a micro or small fluid channel system.

13 Claims, 7 Drawing Sheets

(56) References Cited

U.S. PATENT DOCUMENTS

| | | | |
|---|---|---|---|
| 6,929,239 B1 | 8/2005 | Colin et al. | |
| 6,952,962 B2 * | 10/2005 | Hasselbrink, Jr | F16K 99/0044 73/253 |
| 7,296,592 B2 * | 11/2007 | Rehm | B01L 3/502738 422/68.1 |
| 7,900,888 B2 * | 3/2011 | Weldon | H02K 7/06 251/267 |
| 8,985,547 B2 * | 3/2015 | Weibel | B01L 3/502738 251/8 |
| 2008/0249510 A1 * | 10/2008 | Mescher | A61M 31/002 604/890.1 |
| 2009/0185955 A1 | 7/2009 | Nellissen | |
| 2018/0169654 A1 | 6/2018 | Archibald et al. | |
| 2018/0169655 A1 | 6/2018 | Hartwich et al. | |
| 2020/0164374 A1 | 5/2020 | Zobi et al. | |

FOREIGN PATENT DOCUMENTS

| | | |
|---|---|---|
| CN | 107405621 A | 11/2017 |
| CN | 108223814 A | 6/2018 |
| CN | 109488787 A | 3/2019 |
| CN | 109536364 A | 3/2019 |
| CN | 113266702 A | 8/2021 |
| WO | 2016131537 A1 | 8/2016 |
| WO | 2017030455 A1 | 2/2017 |

OTHER PUBLICATIONS

European Search Report from Corresponding European Patent Application No. EP21914631.3, Nov. 25, 2024.

* cited by examiner

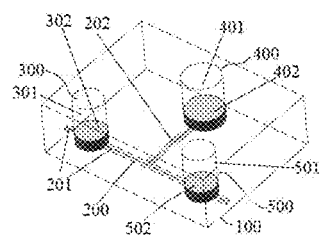
Fig. 2 (a)
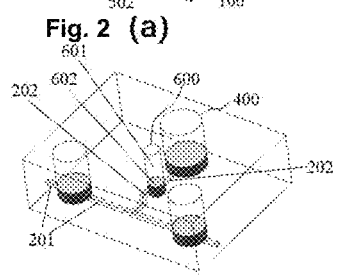
Fig. 2 (b)
Fig. 2
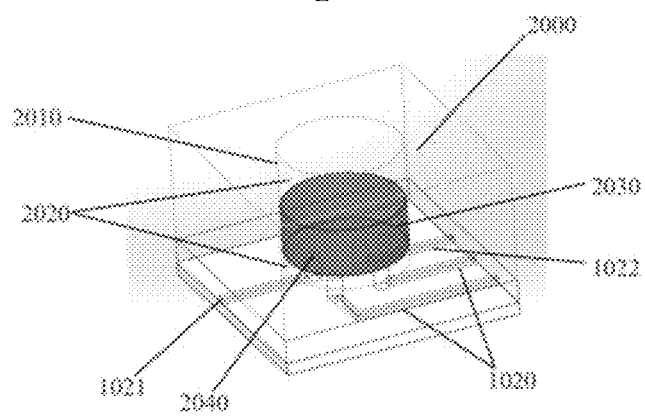
Fig. 3(a)
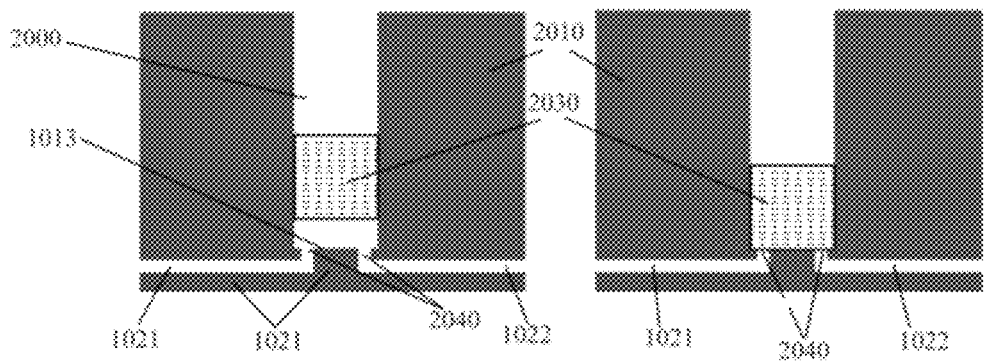
Fig. 3(b)  Fig. 3(c)
Fig. 3

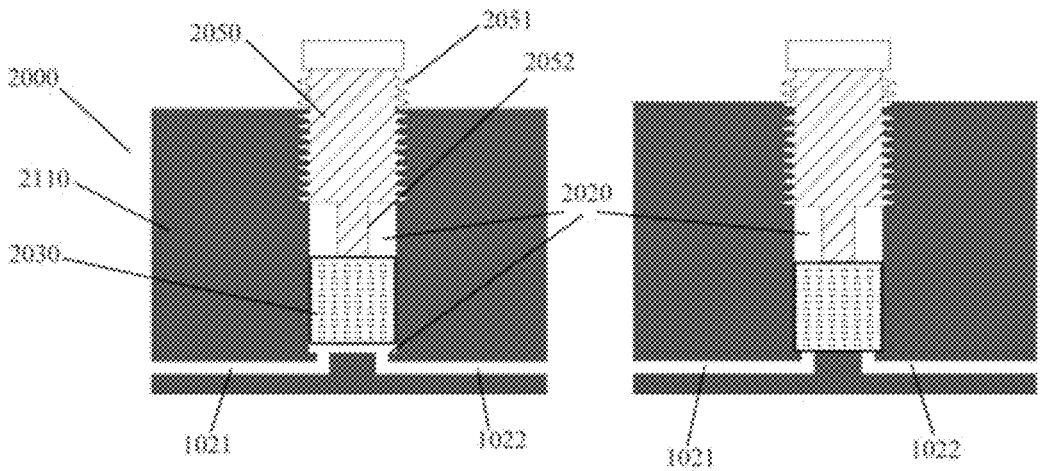
Fig. 4(a)    Fig. 4(b)
Fig. 4
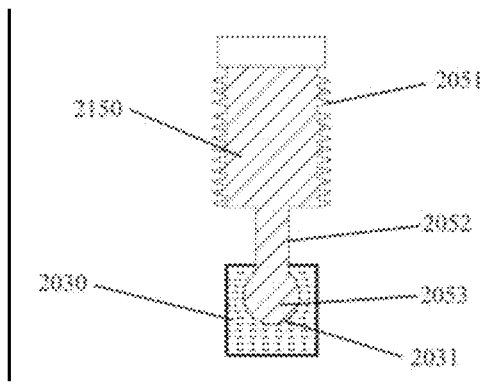
Fig. 5(a)
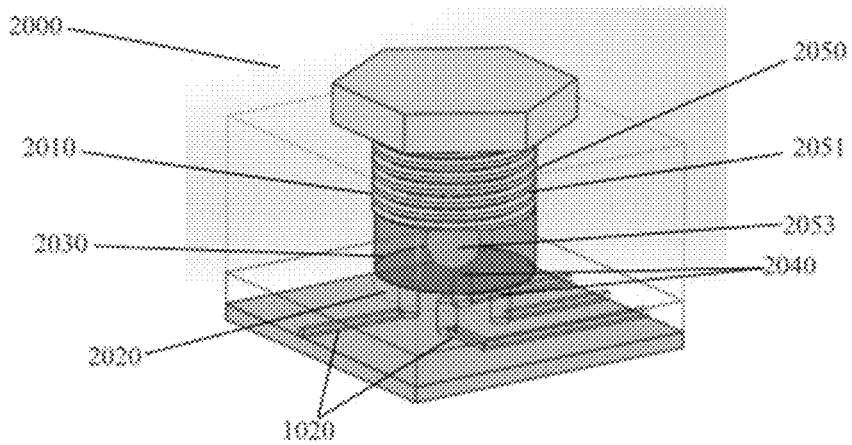
Fig. 5(b)
Fig. 5

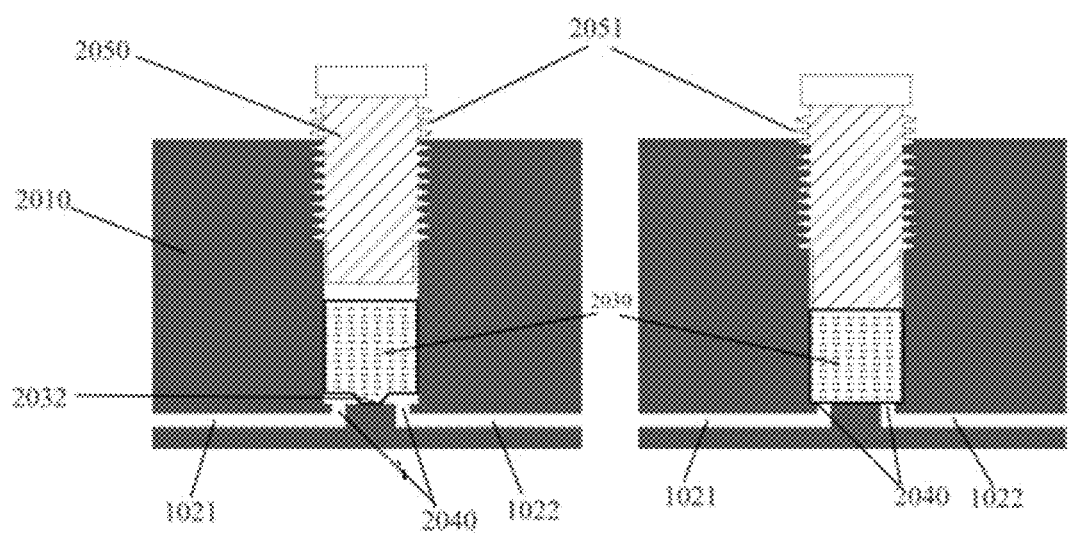
Fig. 6(a)　　　　　Fig. 6(b)
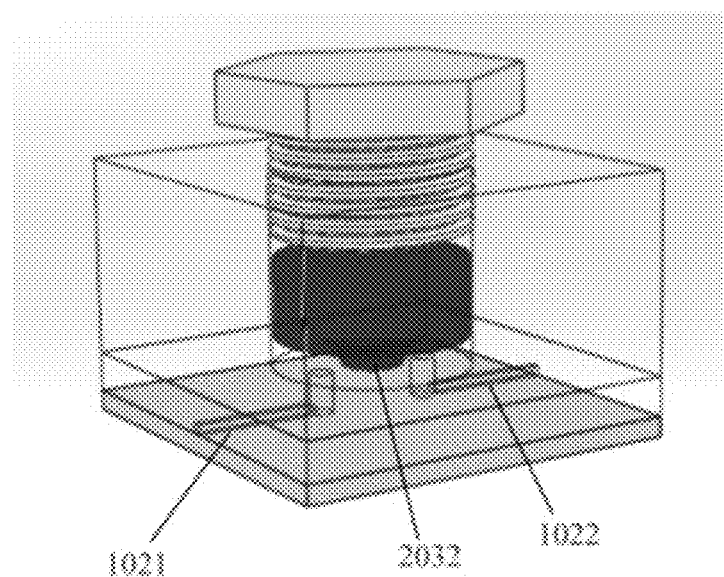
Fig. 6(c)
Fig. 6

Fig. 7(a)
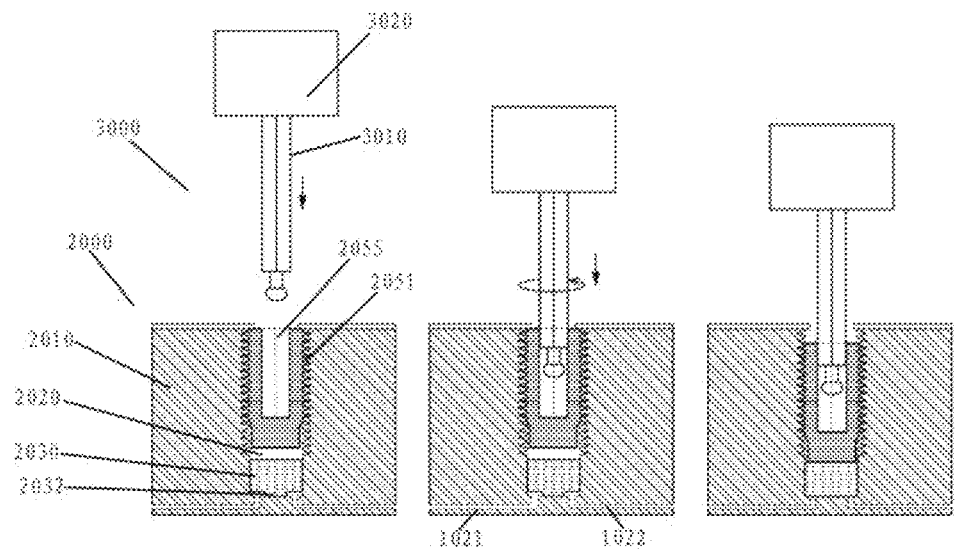
Fig. 7(b)
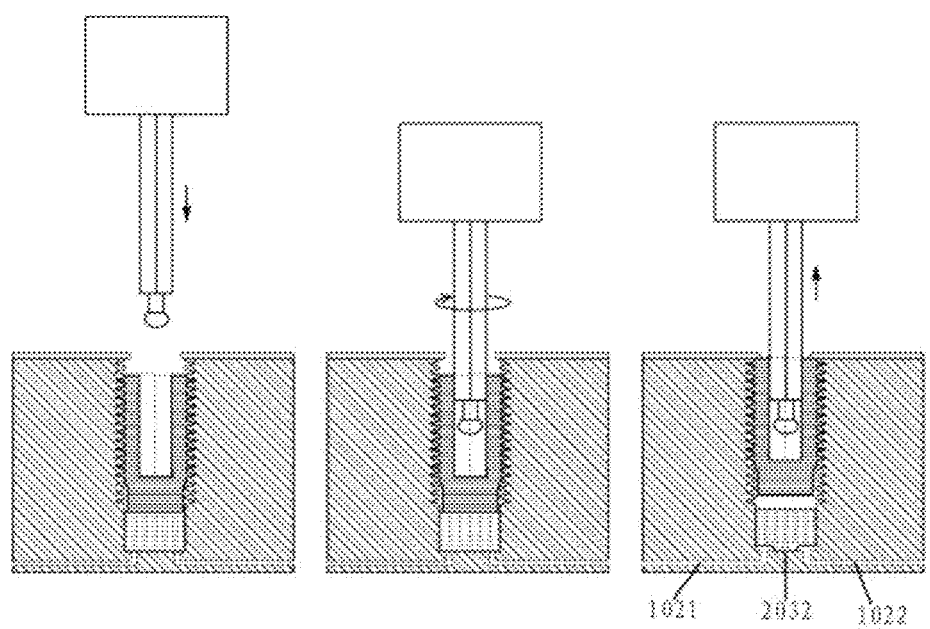
Fig. 7

Fig. 9(a)
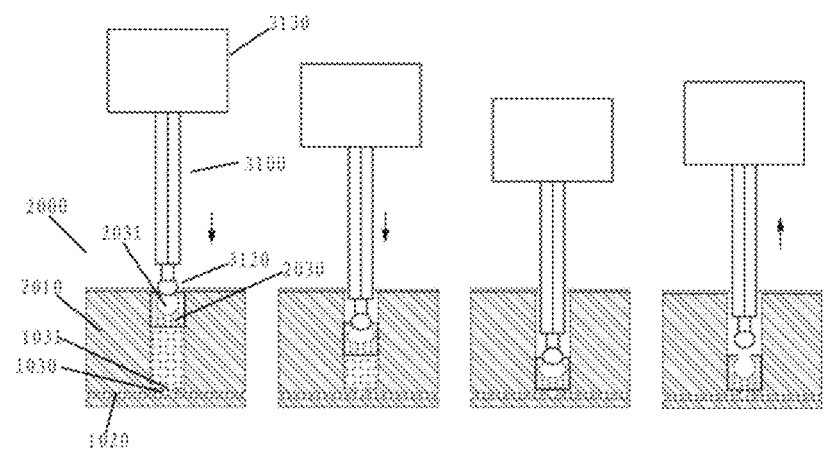
Fig. 9(b)
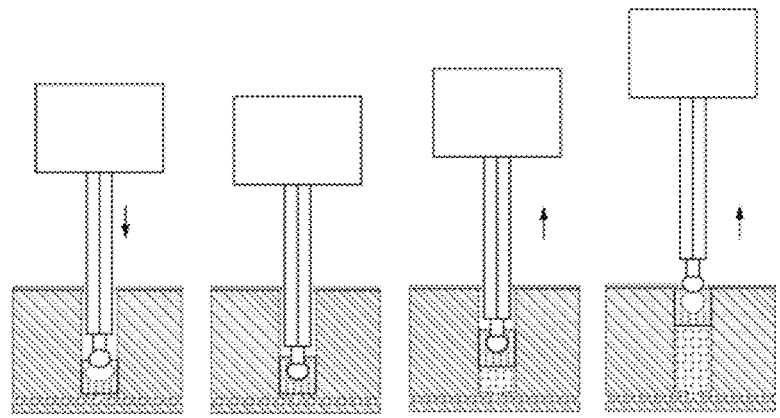
Fig. 9

PISTON MECHANISM, FLUID CONTROL MECHANISM AND APPLICATION THEREOF

The present application claims the priority of Chinese patent application No. 202011639849.5, entitled "piston mechanism, fluid control mechanism and application thereof" and filed on Dec. 31, 2020, the entire content of which is incorporated herein by reference.

TECHNICAL FIELD

The present invention relates to the field of biotechnology and application of related devices, and specifically to a novel piston mechanism and fluid control mechanism, and to a fluid control device comprising the piston mechanism or the fluid control mechanism.

TECHNICAL BACKGROUND

Micro or small fluid channel systems are widely used in a variety of fields including chemistry, biology, healthcare or the like. The control of fluid in the micro or small fluid channel systems is of great significance as the basis for realizing microfluidic applications.

Currently, there are two major problems in the field of fluid control in micro or small fluid channel systems, i.e., power sources and valves. The power source provides power for motion of microfluid within a carrier (e.g., chip, pipe, etc.), and commonly adopts modes including injection, centrifuging, air pressure or the like. Valves are used to control the motion of microfluid within the carrier. Due to the small-scale motion of microfluid, it is rather difficult to construct a sufficient number of valves that are easy to open and close with sufficient precision inside the carrier. Syringe pump is a most commonly used power source, wherein the microfluid is injected into the carrier by drawing the microfluid into the syringe, connecting the syringe to the inlet of the microfluid carrier (hereinafter referred to as "carrier"), and then pushing the syringe with a high-precision syringe pump. However, this operation involves many steps, and the microfluid sample is difficult to switch. Therefore, it is difficult to realize automated injection of microfluid.

There is still a need in the field for mechanisms, devices and methods that can control fluids in the micro or small fluid channel systems more efficiently and conveniently.

SUMMARY OF THE INVENTION

The present invention discloses a fluid control mechanism, comprising: a chamber and a chamber wall, as well as a piston provided within the chamber; and at least one fluid channel, characterized in that a bottom portion of the chamber is configured to be in communication with the fluid channel, wherein an opening connecting the fluid channel and the chamber is arranged at the bottom portion of the chamber, and the piston is configured to be movable to the bottom portion of chamber to cover the opening, thereby blocking the communication between the chamber and the fluid channel.

The above fluid control mechanism according to the present invention is a fluid control device suitable for small and micro fluidic devices, which used to contain and transfer fluid materials, such as liquids, with the fluid channel sized on a millimeter and micron scale, for example, about 0.05-5 mm. When the fluid control device is used in a microfluidic system, for example, a microfluidic control system, the fluid channel thereof is sized on a micron scale. For example, the cross section of the fluid channel has a width of about 0.05-0.5 mm. When the fluid control device is used for a small fluidic system such as a kit, the fluid channel is sized on a millimeter scale. For example, the cross section of the fluid channel has a width of about 0.1-5 mm.

In operation, the fluid channels of the fluid control mechanism according to the present invention are usually arranged horizontally. The chamber is perpendicular to the fluid channels, and the piston is configured to move upward and downward in the chamber. The fluid channels are connected to the bottom portion of the chamber from below through upward openings. Thus the piston can effectively cover the openings connecting the fluid channels and the chamber when moving to the bottom portion of the chamber, thereby blocking fluid communication between the fluid channels and the chamber.

In one aspect of the present invention, the chamber of the above fluid control mechanism is in communication with two or more fluid channels. When not located at the bottom portion of the chamber, the piston does not cover the openings, thus said two or more fluid channels are in fluid communication with each other through the chamber. When the piston moves to the bottom portion of the chamber to cover the openings, the fluid communication between the fluid channels is blocked.

In another aspect of the present invention, the chamber of the above fluid control mechanism is in communication with one fluid channel. When not located at the bottom portion of the chamber, the piston does not cover the opening, thus said fluid channel is in fluid communication with the chamber. When the piston moves to the bottom portion of the chamber to cover the opening, the fluid communication between the fluid channel and the chamber is blocked.

In one aspect of the present invention, the cross section of the fluid channel of the above fluid control mechanism may come in various shapes, including ellipse, rectangle, square, circles, etc. In one aspect of the present invention, the cross section of the fluid channel has a width of about 0.1-5 mm, preferably about 0.2-2 mm, and more preferably about 0.3-1 mm. In one aspect of the present invention, the cross section of the opening connecting the fluid channel and the chamber is usually the same as that of the fluid channel.

In the present invention, a piston of a piston mechanism can be made of rubber, polymer and other materials, which can be deformed to a certain degree, thereby closely fitting with the chamber wall of the piston mechanism to form a closed space that liquid cannot pass through. At the same time, the sound movement of the piston in the chamber can be maintained, and the piston can seal the openings connecting the fluid channels and the chamber when moving to the bottom portion of the chamber under pressure, thereby completely blocking the fluid communication between the fluid channels. In the present invention, the piston is shaped and sized to fit with the chamber. In one aspect of the present invention, the piston has a circular shape, with a diameter of about 0.5-25 mm, preferably about 1-20 mm, and more preferably about 3-15 mm.

In the fluid control device according to the present invention, the movement of the piston in the chamber may be controlled mechanically. For example, the piston is fixedly connected to a connecting rod, so that the position of the piston in the chamber is controlled by pushing and pulling the connecting rod. When the piston moves to the bottom portion of the chamber, pressure may continue to be applied thereto, thereby deforming the piston and sealing the openings connecting the fluid channels and the chamber, so as to completely block the fluid communication between the fluid channels. In other embodiments of the present invention, the movement of the piston may also be controlled in other manners, such as pneumatic or hydraulic manner.

In one aspect of the present invention, the chamber of the above fluid control mechanism further comprises a piston motion control member provided with external threads forming a screw thread pair with internal threads on the chamber wall. The piston motion control member is configured to rotate along the threads to move within the chamber for driving the piston to move in the chamber. The piston motion control member moves in the chamber along the axis thereof when rotating along the threads, i.e., moves upward or downward in the chamber. The fluid control mechanism is arranged so that the piston motion control member can drive the piston to move in the chamber, e.g., to move relative to the chamber in the same manner.

In one aspect of the present invention, a lower end portion of the piston motion control member in the above fluid control mechanism is provided with a piston rod connected to the piston. In another aspect of the present invention, the piston rod is fixedly connected to the piston (e.g., a piston rod and the piston forming into one piece). When the piston motion control member rotates along the threads to move in the chamber, the piston rod drives the piston to move in the chamber. In another aspect of the present invention, a part of the piston rod in contact with the piston is slidably connected to the piston. When the piston motion control member rotates along the threads to move in the chamber, the rotation of the piston rod does not drive the piston to rotate substantially, but only drives the piston to move in the chamber. For example, a bottom portion of the piston rod is provided with a bulge (e.g., a spherical or sphere-like bulge). A notch engageable with the bulge is provided at a top portion of the piston. The piston rod is slidably connected to the piston by inserting the bulge into the notch at the top portion of the piston. In the present invention, the material of the piston has appropriate hardness and elasticity to maintain a fixed shape when subjected to a small force, such as maintaining the shape of the notch to maintain the encircle and restriction of the bulge when the piston rod moves upward and downward, thereby driving the piston to move upward and downward. At the same time, the material of the bulge of the piston rod and that of the piston are selected to generate an appropriate friction force therebetween, so that the rotation of the bulge will not drive the piston to rotate substantially.

In one aspect of the present invention, there is no fixed connection between the piston motion control member and the piston in the above fluid control mechanism. In another aspect of the present invention, a bottom portion of the piston of the piston mechanism is provided with a piston support configured as a bulge and made of elastic material. When the piston support is in a natural state, a part of the piston support in contact with the bottom portion of the piston does not cover the openings connecting the fluid channels and the chamber. When the piston is under pressure (e.g., when the piston motion control member rotates along the threads, moves in the chamber toward the piston, and then contacts with the piston to push it toward the bottom portion of the chamber), the piston support is deformed and compressed so that the entire bottom portion of the piston is in complete contact with the bottom portion of the chamber to cover the openings connecting the fluid channels and the chamber, thereby blocking the communication between the chamber and the fluid channels. When the pressure on the piston disappears (e.g., when the piston motion control member rotates along the threads and moves in the direction away from the piston in the chamber), the piston support returns to its natural state (i.e., the initial state of the piston support without additional pressure on the piston), in which state a part of the piston support in contact with the bottom portion of the piston does not cover any of the openings connecting the fluid channels and the chamber, thereby forming a fluid communication between the fluid channels through the chamber.

In one aspect of the present invention, the chamber of the above fluid control mechanism further comprises a piston motion control member provided with external threads forming a screw thread pair with internal threads on the chamber wall, and configured to rotate along the threads to move in the chamber for controlling the piston to move in the chamber. In the above fluid control mechanism of the present invention, the piston motion control member can be fixedly connected to the piston. In one aspect of the present invention, there is no fixed connection between the piston motion control member and the piston in the above fluid control mechanism. In one aspect of the present invention, the above fluid control mechanism further comprises a manipulation mechanism for controlling the piston motion control member to move. In one aspect of the present invention, the manipulation mechanism is separable from the piston motion control member.

In one aspect of the present invention, the manipulation mechanism comprises a manipulation rod and a manipulation rod motion mechanism. Preferably, the piston motion control member is provided with a chamber suitable for the manipulation rod to insert. After being inserted into the chamber of the piston motion control member, the manipulation rod fits with the chamber and can drive the piston motion control member to rotate when rotating.

In one aspect of the present invention, the manipulation rod motion mechanism comprises a component for controlling upward and downward movement as well as rotation of the manipulation rod, for example, a motor for controlling the rotation of the manipulation rod. Preferably, the motor for controlling the rotation of the manipulation rod is configured as an electric screwdriver, which can set parameters such as rotation direction, rotation speed, rotation angle, stopping torque of the manipulation rod, etc.

In one aspect of the present invention, the manipulation rod is configured as a four- or six-edge screw.

The present invention further discloses a piston mechanism, comprising: a chamber and a chamber wall; and a piston and a piston motion control member provided within the chamber, wherein the piston motion control member is provided with external threads forming a screw thread pair with internal threads on the chamber wall, and is configured to rotate along the threads to move in the chamber for driving the piston to move in the chamber.

According to the present invention, the piston motion control member moves upward or downward in the chamber when rotating along the threads, i.e., moves relative to an axis of the chamber. According to the present invention, the piston mechanism is configured so that the piston motion control member can control the movement of the piston in the chamber, e.g., the movement in the same direction.

In one aspect of the present invention, the chamber of the fluid control mechanism further comprises a piston motion control member provided with external threads forming a screw thread pair with internal threads on the chamber wall and configured to rotate along the threads to move in the chamber and control the piston to move in the chamber. In the above fluid control mechanism of the present invention, the piston motion control member can be fixedly connected to the piston. In one aspect of the present invention, there is no fixed connection between the piston motion control member and the piston in the above fluid control mechanism. In one aspect of the present invention, the above fluid control mechanism further comprises a manipulation mechanism for controlling the piston motion control member to move. In one aspect of the present invention, the manipulation mechanism is separable from the piston motion control member.

In one aspect of the present invention, the manipulation mechanism comprises a manipulation rod and a manipulation rod motion mechanism. Preferably, the piston motion control member is provided with a cavity suitable for receiving the manipulation rod.

In one aspect of the present invention, the manipulation rod motion mechanism comprises a component for controlling upward and downward movement as well as rotation of the manipulation rod, for example, a motor for controlling the rotation of the manipulation rod. Preferably, the motor for controlling the rotation of the manipulation rod is configured as an electric screwdriver, which can set parameters of the manipulation rod, such as rotation direction, rotation speed, rotation angle, stopping torque, etc.

In one aspect of the present invention, the manipulation rod is configured as a four- or six-edge screw.

In one aspect of the present invention, the bottom portion of the chamber of the piston mechanism is in communication with at least one fluid channel, and the opening connecting the fluid channel and the chamber is arranged at the bottom portion of the chamber. The piston can move to the bottom portion of the chamber to cover the opening, thereby blocking the communication between the chamber and the fluid channel. In another aspect of the present invention, the chamber is in communication with two or more fluid channels. When not arranged at the bottom portion of the chamber, the piston does not cover the openings, thus two or more fluid channels are in fluid communication with each other through the chamber of the piston. When the piston moves to the bottom portion of the chamber to cover the openings, the fluid communication between the fluid channels is blocked.

In one aspect of the present invention, the lower end portion of the piston motion control member of the piston mechanism is provided with a piston rod connected to the piston. In another aspect of the present invention, the piston rod is fixedly connected to the piston (e.g., the piston rod and the piston forming into one piece). When the piston motion control member rotates along the threads to move in the chamber, the piston rod drives the piston to move in the chamber. In another aspect of the present invention, a part of the piston rod in contact with the piston is slidably connected to the piston. When the piston motion control member rotates along the threads to move in the chamber, the rotation of the piston rod does not drive the piston to rotate substantially, but only drives the piston to move in the chamber. For example, a bottom portion of the piston rod is provided with a bulge (e.g., a spherical or sphere-like bulge). A notch engageable with the bulge is provided at a top portion of the piston. The piston rod is slidably connected to the piston by inserting the spherical bulge into the notch at the top portion of the piston. In the present invention, the material of the piston has appropriate hardness and elasticity to maintain a fixed shape when subjected to a small force, such as maintaining the shape of the notch to maintain the encircle and restriction of the bulge when the piston rod moves upward and downward, thereby driving the piston to move upward and downward. At the same time, the material of the bulge of the piston rod and that of the piston are selected to generate an appropriate friction force therebetween, so that the rotation of the spherical bulge will not drive the piston to rotate substantially.

In one aspect of the present invention, there is no fixed connection between the piston motion control member and the piston in the piston mechanism. In another aspect of the present invention, the bottom portion of the piston in the piston mechanism is provided with a piston support configured as a bulge and made of elastic material. When the piston support is in a natural state, a part of the piston support in contact with the bottom portion of the piston does not cover the openings connecting the fluid channels and the chamber. When the piston is under pressure (e.g., when the piston motion control member rotates along the threads, moves in the chamber toward the piston, and then contacts with the piston to push it toward the bottom portion of the chamber), the piston support is deformed and compressed so that the entire bottom portion of the piston is in complete contact with the bottom portion of the chamber to cover the openings connecting the fluid channels and the chamber, thereby blocking the communication between the chamber and the fluid channels. When the pressure on the piston disappears (e.g., when the piston motion control member rotates along the threads to moves in a direction away from the piston in the chamber), the piston support returns to its natural state (i.e., the initial state of the piston support without additional pressure on the piston), in which state the part of the piston support in contact with the bottom portion of the piston does not cover any of the openings connecting the fluid channels and the chamber, thereby forming a fluid communication between the fluid channel through the chamber.

The present invention further discloses a fluid control device, comprising a housing, a sample inlet, and at least one aforementioned fluid control mechanism or piston mechanism according to present invention, comprising: a chamber, a chamber wall, a piston provided within the chamber, and at least one fluid channel, characterized in that the bottom portion of the chamber is configured to be in communication with the fluid channel, wherein an opening connecting the fluid channel and the chamber is arranged at the bottom portion of the chamber, and the piston is configured to be movable to the bottom portion of the chamber to cover the opening, thereby blocking the communication between the chamber and the fluid channel.

The fluid control device according to the present invention is suitable for small and micro fluidic devices, which is used to contain and transfer fluid materials such as liquids. When the fluid control device is used in a microfluidic control system, the fluid channel thereof is sized on a micron scale. For example, the cross section of the fluid channel has a width of about 0.05-0.5 mm. When the fluid control device is used for a small fluidic system such as a kit, the fluid channel is sized on a millimeter scale. For example, the cross section of the fluid channel has a width of about 0.1-5 mm.

In another aspect of the present invention, the fluid control device comprises at least one first piston mechanism and at least one second piston mechanism, wherein the first piston mechanism and the second piston mechanism comprise a first chamber and a second chamber, respectively, in communication with fluid channels. The first chamber and the second chamber comprise a first piston and a second piston, respectively, wherein the first piston makes a first movement relative to the first chamber and the second piston makes a second movement relative to the second chamber. Due to the first and second movements, the first and the second pistons cause the same volume change in the first and second chambers, but with opposite effects. The first piston mechanism and the second piston mechanism are configured so that the pistons thereof can move to positions blocking the fluid channels, wherein one or more of at least one first piston mechanism and at least one second piston mechanism is configured in the same manner as in the aforementioned fluid control mechanism. For example, the bottom portion of the first or the second chamber is in communication with at least one fluid channel, wherein the opening connecting the fluid channel to the first or the second chamber is arranged at a bottom portion of the chamber. The first or the second piston is configured to be movable to the bottom portion of the chamber to cover the openings, thereby blocking the communication between the chamber and the fluid channel.

In another aspect of the present invention, a piston valve mechanism is provided between one or both of the first and the second piston mechanisms and the fluid channels in the fluid control device. The piston valve mechanism includes a valve chamber in communication with the fluid channels and a valve piston provided in the valve chamber. The valve piston can move to positions blocking the openings in communication with the fluid channels, thereby closing the fluid channels, wherein at least one piston valve mechanism is configured in the same manner as in the aforementioned fluid control mechanism. For example, a bottom portion of the valve chamber is in communication with at least one fluid channels, wherein the openings connecting the fluid channel to the valve chamber is arranged at a bottom portion of the valve chamber. The valve piston is configured to be movable to the bottom portion of the valve chamber to cover the opening, thereby blocking the communication between the valve chamber and the fluid channel.

In one aspect of the present invention, the fluid control device is adapted to contain liquid material, gaseous material, emulsion material, slurry material, fluid material in which solid material is dissolved, and fluid material in which solid particles are suspended.

In one aspect of the present invention, the fluid control device is configured as a kit which can be used for infection source identification, genetic disease detection, cancer detection, or genetic variant detection. In one aspect of the present invention, the kit can be used to detect biologically active substances in a sample, such as nucleic acids or proteins. The kit includes containing spaces for containing samples or various reaction reagents, or for performing various reactions. The samples or various reaction reagents can flow in a fluid form between various containing spaces. Said reactions include lysis of tissues or cells in the sample, enrichment or extraction of nucleic acid or protein samples, amplification reactions of nucleic acids, and detection of nucleic acids, amplification products thereof or signals carried by nucleic acids, etc.

The present invention further discloses a small fluid control device, comprising a housing and a sample inlet, at least one fluid channel, at least one aforementioned piston mechanism according to the present invention, comprising: a chamber and a chamber wall; a piston and a piston motion control member provided within the chamber, wherein the piston motion control member is provided with external threads forming a screw thread pair with internal threads on the chamber wall, and is configured rotate along the threads to move in the chamber for driving the piston to move in the chamber.

In another aspect of the present invention, the small fluid control device comprises at least one first piston mechanism and at least one second piston mechanism, wherein the first piston mechanism and the second piston mechanism comprise a first chamber and a second chamber, respectively, in communication with fluid channels. The first chamber and the second chamber comprise a first piston and a second piston, respectively, wherein the first piston makes a first movement relative to the first chamber and the second piston makes a second movement relative to the second chamber. Due to the first and second movements, the first and the second pistons cause the same volume change in the first and second chambers, but with opposite effects. The first piston mechanism and the second piston mechanism are configured so that the pistons thereof can move to positions in the chambers thereof blocking the communication with the fluid channels, wherein one or more of at least one first piston mechanism and at least one second piston mechanism is configured in the same manner as in the aforementioned piston mechanism. For example, the bottom portion of the first or the second chamber is in communication with at least one fluid channel, wherein the opening connecting the fluid channel to the first or the second chamber is arranged at a bottom portion of the chamber. The first or the second piston is configured to be movable to the bottom portion of the chamber to cover the opening, thereby blocking the communication between the chamber and the fluid channel.

In another aspect of the present invention, a piston valve mechanism is provided between one or both of the first and the second piston mechanisms and the fluid channels in the small fluid control device. The piston valve mechanism includes a valve chamber in communication with the fluid channels and a valve piston provided in the valve chamber. The valve piston can move to positions blocking the openings in communication with the fluid channels, thereby closing the fluid channels, wherein at least one piston valve mechanism is configured in the same manner as in the aforementioned piston mechanism. For example, a bottom portion of the valve chamber is in communication with at least one fluid channel, wherein the opening connecting the fluid channel to the valve chamber is arranged at the bottom portion of the valve chamber. The valve piston is configured to be movable to the bottom portion of the valve chamber to cover the opening, thereby blocking the communication between the valve chamber and the fluid channel.

In one aspect of the present invention, the small fluid control device is adapted to contain liquid material, gaseous material, emulsion material, slurry material, fluid material in which solid material is dissolved, and fluid material in which solid particles are suspended.

In one aspect of the present invention, the small fluid control device is configured as a kit which can be used for infection source identification, genetic disease detection, cancer detection, or genetic variant detection. In one aspect of the present invention, the kit can be used to detect biologically active substances in a sample, such as nucleic acids or proteins. The kit includes containing spaces for containing samples or various reaction reagents, or for performing various reactions. The samples or various reaction reagents can flow in a fluid form between various containing spaces. Said reactions include lysis of tissues or cells in the sample, enrichment or extraction of nucleic acid or protein samples, amplification reactions of nucleic acids, and detection of nucleic acids, amplification products thereof or signals carried by nucleic acids, etc.

BRIEF DESCRIPTION OF THE DRAWINGS

In order to illustrate the technical solutions in the embodiments of the present invention or in the prior arts more clearly, a brief description of the drawings required in the embodiments or the prior arts is provided below. It would be apparent that the drawings introduced below are some embodiments of the present invention, and one skilled in the art may conceive other drawings on the basis of these drawings without creative labor.

FIGS. 1(a) to 1(i), shows a structure of an exemplary fluid control device and a working process thereof. Specifically, FIGS. 1(a) to (f) show the structure and working process of the fluid control device according to the present application.

FIG. 2, including FIGS. 2(a) and 2(b), schematically shows a three-dimensional structure of an exemplary fluid control device with fluid storage and output units. Specifically, FIG. 2(a) shows one exemplary fluid control device with fluid storage and output units according to the present application, while FIG. 2(b) shows another exemplary fluid control device with fluid storage and output units according to the present application.

FIG. 3, including FIGS. 3(a) to 3(c), schematically shows a structure of another exemplary fluid control device. Specifically, FIG. 3(a) is a perspective view schematically showing the structure of the fluid control device, while FIGS. 3(b) and 3(c) are sectional views of the exemplary fluid control device shown in FIG. 3(a), which show two working states, respectively.

FIG. 4, including FIGS. 4(a) and 4(b), shows sections of a piston mechanism employed in another exemplary fluid control device according to the present invention. Specifically, FIGS. 4(a) and 4(b) show two working states, respectively.

FIG. 5, including FIGS. 5(a) and 5(b), schematically shows another exemplary fluid control device according to the present invention. Specifically, FIG. 5(a) shows a partial section of a piston mechanism employed in the exemplary fluid control device, while FIG. 5(b) is a perspective view schematically showing the exemplary fluid control device according to the present invention.

FIG. 6, including FIGS. 6(a) to 6(c), schematically shows another exemplary fluid control device according to the present invention. Specifically, FIGS. 6(a) and 6(b) are sectional views of the exemplary fluid control device, which show two working states, respectively, while FIG. 6(c) is a perspective view schematically showing the structure of the exemplary fluid control device according to the present invention, which shows a working state as shown in FIG. 6(a).

FIG. 7, including FIGS. 7(a) and 7(b), shows sectional views of another exemplary fluid control device and a piston mechanism employed therein according to the present invention, illustrating the working states thereof.

FIG. 9, including FIGS. 9(a) and 9(b), shows sectional views of another exemplary fluid control device and a piston mechanism employed therein according to the present invention, illustrating the working states thereof.

DETAILED DESCRIPTION OF EMBODIMENTS

In order to illustrate the purpose, the technical solutions and the advantages of the embodiments of the present invention more clearly, the technical solutions in embodiments of the present invention will be explained clearly in full detail with reference to the accompanying drawings. It is obvious that the embodiments illustrated herein are a part of the embodiments of the present invention, rather than all of them. Any other embodiments obtained by one skilled in the art without creative labor on the basis of the embodiments of the present invention all fall within the scope of protection of the present invention.

First Embodiment

A fluid control device is illustrated in Chinese patent application No. 202010092879.2 of the applicant, and the application which claims the priority thereof. The fluid control device shown can be used in a micro or small fluid channel system such as a microfluidic device or a kit, wherein different combinations of multiple piston mechanisms are adopted to achieve fluid injection or storage, as well as to control the direction/flow of fluid. The application is incorporated herein in its entirety as part of the description of the present invention, or as a cross-reference to the technical solutions provided by the present invention.

Figure 1:
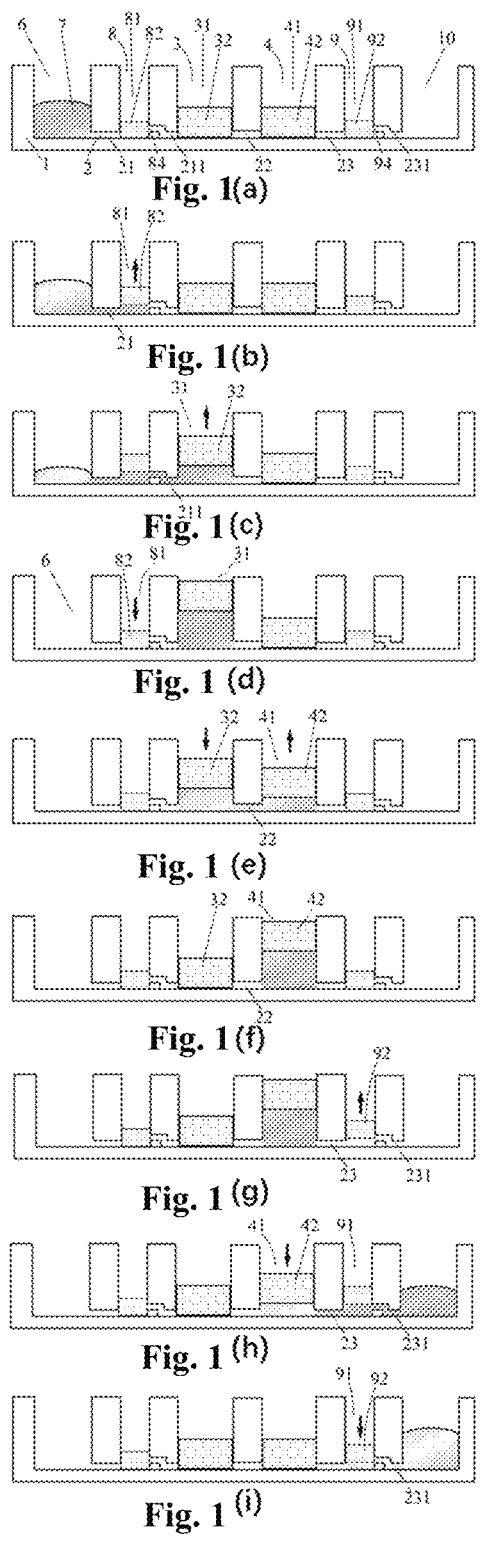
FIG. 1, including

FIG. 1 schematically shows the structure of a fluid control device according to the present application, and the working process thereof. As shown in FIG. 1(a), the fluid control device is provided with a fluid channel 2. A wall 1 of the fluid channel includes a side wall and a bottom portion of the fluid channel.

The fluid control device adopts two or more piston mechanisms to control the flow of fluid (to be stationary or moving), as well as the flow direction and/or flow rate thereof. The exemplary fluid control device in FIG. 1 includes a piston mechanism 3 and a piston mechanism 4 comprising a chamber 31 and a chamber 41, respectively, which are both connected to the fluid channel 2. A piston 32 and a piston 42 are provided in the chamber 31 and the chamber 41, respectively. The fluid control device may include two or more piston mechanisms.

In the fluid control device illustrated in FIG. 1, the movement of the piston may be controlled pneumatically. In other embodiments, the movement of the piston may be controlled mechanically. For example, the pistons 32 and/or 42 are fixedly connected to a piston connecting rod, which can be pushed and pulled to control the position and movement of the pistons in the chambers. In the exemplary fluid control device in FIG. 1 according to the present invention, the pistons 32 and/or 42 may be pushed to the bottom portion of the fluid channel 2 in order to block the fluid channel.

When the fluid control device illustrated in FIG. 1 is in operation, the piston mechanisms 3 and 4 operate simultaneously, wherein the two pistons arranged therein move simultaneously but in opposite directions, causing the same volume changes in the corresponding chambers, but with opposite effects. That is, the volume of a chamber in one piston mechanism increases, while that in the other piston mechanism decreases. In one aspect of the present invention, the pistons of the two or more piston mechanisms have the same cross sections, whereby the two piston mechanisms control the respective pistons to move at the same speed when operating simultaneously, causing the same volume changes in the corresponding chambers, but with opposite effects.

The fluid control device illustrated in FIG. 1 further comprises a valve between one or both of the piston mechanisms 3, 4 and the fluid channel. The fluid communication between the piston mechanisms and the fluid channel is controlled by the valve. For example, the valve can block or partially block the fluid communication between the piston mechanisms and the fluid channel. In the fluid control device illustrated in FIG. 1, the valve is configured as a piston mechanism. A piston valve mechanism 8 is provided upstream of the piston mechanism 3, and includes a valve chamber 81 comprising a valve piston 82 therein. The valve chamber 81 is in communication with the chamber 31 through a valve fluid channel 211. An opening 84 of the fluid channel 211 in the valve chamber 81 is arranged on the wall of the chamber, i.e., the opening is arranged at a position above the fluid channel 2. The valve piston 82 can be pushed to the bottom portion of the fluid channel 2, blocking the fluid channel. In addition, the thickness of the valve piston 82 is greater than the width of the opening 84, so that the valve piston 82 can block the opening 84 sufficiently to close the fluid channel between the valve chamber 81 and the chamber 31.

In the fluid control device illustrated in FIG. 1, a piston valve mechanism 9 is provided downstream of the piston mechanism 4, and includes a valve chamber 91 comprising a valve piston 92 therein. The valve chamber 91 is in communication with an outlet fluid channel 10 through a valve fluid channel 231. The valve fluid channel 231 is provided with an opening 94 in the valve chamber 91 arranged on a wall of the chamber at a position above the bottom portion of the fluid channel. The valve piston 92 and the opening 94 are arranged so that the opening 94 can be completely blocked to close the fluid channel when the valve piston 92 is pressed down.

The working process of the fluid control device illustrated in FIG. 1 is shown in FIG. 1(*a*) to FIG. 1(*i*).

FIG. 2 schematically shows a three-dimensional structure of an exemplary fluid control device with fluid storage and output units.

The fluid control device shown in FIG. 2(*a*) includes a housing 100, and a fluid channel 200 comprising a main channel 201 and a branch channel 202. The fluid control device comprises three piston mechanisms 300, 400 and 500, wherein the piston mechanisms 300 and 500 are arranged on the main channel 201 and the piston mechanism 400 is arranged at an end portion of the branch channel 202. In this exemplary fluid control device, the fluid can enter a chamber 401 of the piston mechanism 400 from the piston mechanism 300 via the main channel 201 and the branch channel 202, similar to the process shown in FIG. 1 concerning achieving fluid injection or storage by controlling the movement of the pistons. By pressing down a piston 302 of the piston mechanism 300 and pulling up a piston 402 of the piston mechanism 400 at the same time, for example, the fluid to be stored can enter the chamber 401 of the piston mechanism 400 from a chamber 301 of the piston mechanism 300 via the main channel 201 and the branch channel 202, wherein the volume of the stored fluid can be adjusted through a distance travelled by the piston 402 when pulled up according to needs. In this exemplary fluid control device, the fluid to be stored can enter the chamber 401 of the piston mechanism 400 directly from an input opening via the main channel 201 and the branch channel 202 by pulling up the piston 402 of the piston mechanism 400 while keeping the piston 302 of the piston mechanism 300 fixed not to impede the flow in the main fluid channel.

Similarly, the fluid can move or stay in the chamber 401 of the piston mechanism 400 and the chamber 501 of the piston mechanism 500 or the fluid channel therebetween through operations on the pistons 402 and 502.

On the basis of the exemplary fluid control device illustrated in FIG. 2(*a*), FIG. 2(*b*) shows a further exemplary fluid control device, wherein a piston valve mechanism 600 is further provided on the branch channel 202, i.e., between the piston mechanism 400 and the main channel 201. The piston valve mechanism 600 is provided with a valve chamber 601 comprising a valve piston 602 therein, which can be pushed to a bottom portion of the branch channel 202 to block the fluid channel. In the exemplary fluid control device shown in FIG. 2(*b*), the branch channel 202 connected to the main channel 201 has an opening on a wall of the valve chamber 601 (i.e., forming a valve fluid channel connecting the piston valve mechanism 600 and the fluid channel). The branch channel 202 connected to the main channel 201 and/or the branch channel 202 connected to the piston valve mechanism 600 has an opening on the wall of the valve chamber 601.

In the fluid control device illustrated in FIG. 1 and FIG. 2, the openings connecting the piston mechanism and the piston valve mechanism to the fluid channel, and those connecting the piston mechanism to the piston valve mechanism are all arranged on the wall of the chamber. For example, the openings connecting the piston mechanisms 3 and 4 to the fluid channels in FIG. 1(*a*), and those connecting the piston mechanisms 300 and 400 to the fluid channels in FIG. 2(*a*) are all arranged on a wall at the bottom portion of the chamber. For another example, the channel openings connecting the piston valve mechanism 8 to the piston mechanism 3 in FIG. 1(*a*), and those connecting the piston valve mechanism 600 to the fluid channel 202 in FIG. 2(*a*) are all arranged on the wall of the valve chamber at a position above the bottom portion of the fluid channel.

Second Embodiment

The present invention provides a piston mechanism for a micro or small fluid channel system such as a microfluidic device or a kit, and a fluid control device using the same.

FIG. 3 schematically shows a structure of an exemplary fluid control device according to the present invention. FIG. 3(*a*) is a perspective view schematically showing the fluid control device. As shown in FIG. 3(*a*), one embodiment of the present invention provides a fluid control device comprising a plurality of fluid channels 1020, which are provided at a bottom portion thereof. A wall 1010 of the fluid channel 2 (including a sidewall 1011 and a bottom portion 1012, etc.) is made from materials including, but not limited to, silica, silicon, quartz, glass, or polymeric materials (e.g., PDMS, plastic, etc.). The fluid control device according to the present invention suitable for small and micro fluidic devices is used to contain and transfer fluid materials, such as liquids, with the fluid channel sized on a millimeter and a micron scale, for example, about 0.05-5 mm. When the fluid control device is used in a microfluidic system, the fluid channel thereof is sized on a micron scale. For example, the cross section of the fluid channel has a width of about 0.05-0.5 mm. In one aspect of the present invention, the cross section of the fluid channel has a width of about 0.05-0.5 mm, preferably about 0.05-0.2 mm. When the fluid control device is used for a small fluidic system such as a kit, the fluid channel is sized on a millimeter scale. For example, the cross section of the fluid channel has a width of about 0.1-5 mm. In one aspect of the present invention, the cross section of the fluid channel may come in various shapes, including ellipse, rectangle, square, circles, etc. In one aspect of the present invention, the cross section of the fluid channel has a width of about 0.1-5 mm, preferably about 0.2-2 mm.

The fluid control device is provided with a piston mechanism 2000 comprising a chamber wall 2010, a chamber 2020 formed by a space defined by the chamber wall, and a piston 2030 movable within the chamber. As shown in FIG. 3(*a*), a bottom portion of the chamber 2020 is in communication with the plurality of fluid channels, and openings 2040 connecting the fluid channels to the chamber are all arranged at the bottom portion of the chamber of the piston mechanism. The piston 2030 can move to the bottom portion of the chamber of the piston mechanism to cover the openings 2040 connecting the fluid channels to the chamber, thus blocking the communication between the fluid channels and the chamber. When the piston is not located at the bottom portion of the chamber, the piston does not cover the openings, thereby allowing the fluid communication between the fluid channels through the chamber. When the piston moves to the bottom portion of the chamber to cover the openings, the fluid communication between the fluid channels is blocked.

In the present invention, the piston of the piston mechanism can be made of rubber, polymer and other materials, which can be deformed to a certain degree, thereby closely fitting with the wall of the chamber of the piston mechanism to form a closed space that liquid cannot pass through. At the same time, the sound movement of the piston in the chamber can be maintained, and the piston can seal the openings connecting the fluid channels and the chamber when moving to the bottom portion of the chamber under pressure, thereby completely blocking the fluid communication between the fluid channels. In the present invention, the piston is shaped and sized to fit with the chamber. In one aspect of the present invention, the piston has a circular shape, with a diameter of approximately 1-30 mm, preferably 5-20 mm.

In the present invention, the material forming the chamber wall of the piston mechanism is generally the same as that of wall of the fluid channels.

As shown in FIG. 3($a$), the chamber 2020 can be in communication with a plurality of fluid channels 1020. The openings 2040 connecting the fluid channels and the chamber are all arranged at the bottom portion of the chamber, wherein the fluid channels 1021 and 1022 are arranged on the same level.

FIGS. 3($b$) and 3($c$) are cross-sectional views of the exemplary fluid control device shown in FIG. 3($a$) through fluid channels 1021 and 1022 respectively. The fluid channels are defined by the fluid channel sidewall 1011 and the bottom portion 1012. The openings 2040 connecting the fluid channels and the chamber are all arranged at the bottom portion of the chamber, and the top portion 1013 of the fluid channel sidewall forms a part of the bottom portion of the chamber. As shown in FIG. 3($b$), the piston does not cover the openings when not located at the bottom portion of the chamber, thus a plurality of fluid channels (including fluid channels 1010 and 1022) are in fluid communication with each other through the chamber. As shown in FIG. 3($c$), the fluid communication between the fluid channels is blocked when the piston moves to the bottom portion of the chamber to cover the openings.

In the fluid control device according to the present invention, the movement of the piston in the chamber may be controlled mechanically. For example, the piston is fixedly connected to a connecting rod, so that the position of the piston in the chamber is controlled by pushing and pulling the connecting rod. When the piston moves to the bottom portion of the chamber, pressure may continue to be applied thereto, thereby deforming the piston and sealing the openings connecting the fluid channels and the chamber, so as to completely block the fluid communication between the fluid channels. In other embodiments of the present invention, the movement of the piston may also be controlled in other manner, such as pneumatic or hydraulic manner.

FIG. 4 shows a cross section of a piston mechanism employed in another exemplary fluid control device according to the present invention, wherein the piston mechanism 2000 comprises a chamber wall 2010, a chamber 2020 formed by a space defined by the chamber wall, a piston 2030 movable within the chamber, and a piston motion control member 2050 for controlling the movement of the piston. According to the exemplary piston mechanism shown in FIG. 4, the piston motion control member 2050 is provided with external threads 2051 to form a screw thread pair with internal threads on the chamber wall 2010. When rotating along the threads, the piston motion control member 2050 moves upward or downward within the chamber 2020, i.e., moving relative to an axis of the chamber. According to the exemplary piston mechanism shown in FIG. 4, a lower end portion of the piston motion control member is provided with a piston rod 2052 fixedly connected to the piston 2030. In one embodiment of the present invention, the piston motion control member (including the piston rod 2052) and the piston 2030 form an integrated part. When the piston motion control member 2050 rotates along the threads to move upward or downward within the chamber 2020, the piston is driven to move in the same manner within the chamber through the piston rod.

As shown in FIG. 4($a$), the piston does not cover the openings when not located at the bottom portion of the chamber, thus the plurality of fluid channels (including fluid channels 1021 and 1022) is in fluid communication with each other through the chamber. As shown in FIG. 4($b$), the fluid communication between the fluid channels is blocked when the piston moves to the bottom portion of the chamber to cover the openings.

FIG. 5 schematically shows another exemplary fluid control device according to the present invention. FIG. 5($a$) shows a partial cross section of a piston mechanism employed in the exemplary fluid control device, wherein the piston motion control member 2050 is provided with external threads 2051 to form a screw thread pair with internal threads of the chamber wall of the piston (not shown). When rotating along the threads, the piston motion control member 2050 moves upward or downward within the chamber of the piston (not shown). According to the exemplary piston mechanism shown in FIG. 5, a piston rod 2052 arranged at a lower end portion of the piston motion control member is provided with a spherical bulge 2053 at a bottom portion thereof. A notch 2031 engageable with the spherical bulge 2053 is provided at a top portion of the piston 2030. The piston motion control member is slidably connected to the piston by inserting the spherical bulge 2053 at the bottom portion of the piston rod into the notch 2031 at the top portion of the piston 2030. The material of the piston has appropriate hardness and elasticity to maintain a fixed shape when subjected to a small force, such as maintaining the shape of the notch to maintain the encircle and restriction of the spherical bulge when the piston rod moves upward and downward in the chamber, thereby driving the piston to move upward and downward in the chamber. At the same time, the material of the spherical bulge of the piston rod and that of the piston are selected to generate a suitable friction force therebetween, so that the rotation of the spherical bulge will not drive the piston to rotate substantially. Thus, when the piston motion control member 2050 rotates along the threads to move upward or downward in the chamber 2020, the piston is driven by the spherical bulge 2053 at the bottom portion of the piston rod to move upward or downward in the same manner in the chamber.

FIG. 5(b) is a perspective view of the exemplary fluid control device according to the present invention. As shown in FIG. 5(b), the piston rod at a lower end portion of the piston motion control member 2050 of the piston mechanism 2000 is provided with a spherical bulge 2053 at a bottom portion thereof. The piston 2030 is provided with a notch 2031 engageable with the spherical bulge 2053. The piston motion control member is movably connected to the piston by inserting the spherical bulge 2053 at the bottom portion of the piston rod into the notch 2031 at the top portion of the piston 2030. The piston motion control member 2050 is provided with external threads 2051 to form a screw thread pair with internal threads on the chamber wall 2010 of the piston. When rotating along the threads, the piston motion control member 2050 moves upward or downward within the chamber 2020 of the piston. A bottom portion of the chamber 2020 is in communication with the plurality of fluid channels 1020, and the openings 2040 connecting the fluid channels to the chamber are all arranged at the bottom portion of the chamber of the piston. The piston 2030 that is driven by the piston motion control member 2050 moves to the bottom portion of the chamber of the piston to cover the openings 2040 connecting the fluid channels to the chamber, thereby blocking the fluid communication.

FIG. 6 schematically shows another exemplary fluid control device according to the present invention. FIGS. 6(a) and 6(b) are sectional views of the exemplary fluid control device. According to FIGS. 6(a) and 6(b), the fluid control device is provided with a piston mechanism 2000, comprising a chamber wall 2010, a chamber 2020 formed by a space defined by the chamber wall, and a piston 2030 movable within the chamber. The piston motion control member 2050 is provided with external threads 2051 to form a screw thread pair with internal threads on the chamber wall 2010 of the piston. When rotating along the threads, the piston motion control member 2050 moves upward or downward within the chamber of the piston. According to the exemplary piston mechanism shown in FIG. 6, there is no fixed connection between the piston motion control member and the piston 2030. A bottom portion of the piston is provided with a piston support 2032, which is configured as a bulge at the bottom of the piston and made of elastic material which will be compressed due to deformation under pressure. When the piston is under pressure (e.g., when the piston motion control member rotates along the threads, moves in the chamber toward the piston, and then contacts with the piston to push it toward the bottom portion of the chamber), the piston support is flattened so that the entire bottom portion of the piston is in complete contact with the bottom portion of the chamber to cover all the openings 2040 connecting the fluid channels (e.g., fluid channels 1021 and 1022 as shown) with the chamber, thereby blocking the fluid communication between the fluid channels (as shown in FIG. 6(b)). When the pressure on the piston disappears (e.g., when the piston motion control member rotates along the threads and moves in the direction away from the piston in the chamber), the piston support 2032 returns to its natural state (i.e., the initial state of the piston support 2032 without additional pressure on the piston), in which state the piston support lifts the piston up, so that the area where the bottom portion of the piston is in contact with the bottom portion of the chamber (i.e., the area where the piston support is located) does not cover any of the openings 2040 connecting the fluid channels and the chamber, thereby allowing fluid communication between the fluid channels through the chamber (as shown in FIG. 6(a)).

FIG. 6(c) is a perspective view of the exemplary fluid control device according to the present invention, which shows the operation state as shown in FIG. 6(a). That is, when the pressure on the piston disappears (e.g., when the piston motion control member rotates along the threads and moves in the direction away from the piston in the chamber), the piston support 2032 returns to its natural state (i.e., the initial state of the piston support 2032 without additional pressure on the piston). As can be clearly seen from the perspective view, a fluid communication between the fluid channels through the chamber is formed when the piston support 2032 is in its natural state, since the area where the piston support is in contact with the bottom portion of the piston does not cover any of the openings 2040 connecting the fluid channels and the chamber.

FIG. 7 schematically shows another exemplary fluid control device according to the present invention. FIGS. 7(a) and 7(b) are sectional views of the exemplary fluid control device. As shown in FIGS. 7(a) and 7(b), the fluid control device is provided with a piston mechanism 2000, comprising a chamber wall 2010, a chamber 2020 formed by a space defined by the chamber wall, and a piston 2030 movable within the chamber. The piston motion control member 2050 is provided with external threads 2051 to form a screw thread pair with internal threads on a chamber wall 2010 of the piston. When rotating along the threads, the piston motion control member 2050 moves upward or downward within the chamber of the piston. According to the exemplary piston mechanism shown in FIG. 7, the movement of the piston motion control member 2050 is adjusted by a manipulation mechanism 3000 thereof. As shown in FIG. 7(a), the manipulation mechanism comprises a manipulation rod 3010 and a manipulation rod motion mechanism. The manipulation rod can be rotated or moved upward and downward. The piston motion control member is provided with a cavity suitable for receiving the manipulation rod, which fits with the cavity when inserted therein, so that the rotation of the manipulation rod and can drive the piston motion control member to rotate. The manipulation rod motion mechanism comprises a component for controlling upward and downward movement and rotation of the manipulation rod, for example, a motor for controlling the rotation of the manipulation rod as shown in the drawing. In the present invention, the manipulation rod motion motor may be an electric screwdriver 3020, which can set parameters of the manipulation rod, such as rotation direction, rotation speed, rotation angle, stopping torque, etc. The piston motion control member 2050 is provided with a cavity 2055 suitable for receiving the manipulation rod, wherein a cross section of the cavity has a shape adapted to that of the manipulation rod (e.g., a four- or six-edge screw in the embodiment shown in FIG. 7). FIG. 7(a) schematically shows the piston motion control member is controlled to move downward. As shown in FIG. 7(a), clockwise rotation of the manipulation rod after inserted into the cavity of the piston motion control member can drive the piston motion control member 2050 to rotate along the threads and move downward in the chamber 2020. In one aspect of the present invention, the manipulation rod may be inserted into the cavity of the piston motion control member in a slowly rotating manner. The insertion while rotating allows the edges of the manipulation rod to engage with the interior of the cavity, effectively solving the alignment problem. In the exemplary piston mechanism shown in FIG. 7, there is no fixed connection between the piston motion control member and the piston 2030. The bottom portion of the piston is provided with a piston support 2032, which is configured as a bulge at the bottom of the piston and made of elastic material which will be compressed due to deformation under pressure. When the piston is under pressure (e.g., when the piston motion control member rotates along the threads, moves in the chamber toward the piston, and then contacts with the piston to push it toward the bottom portion of the chamber), the piston support is flattened so that the bottom portion of the piston is entirely in complete contact with the bottom portion of the chamber to cover all the openings 2040 connecting the fluid channels (e.g., fluid channels 1021 and 1022 as shown) with the chamber, thereby blocking the fluid communication between the fluid channels (as shown in FIG. 7 (a)). When the pressure on the piston disappears, the piston support 2032 returns to its natural state, in which state the piston support enables the area where the bottom portion of the piston is in contact with the bottom portion of the chamber not to cover any of the openings 2040 connecting the fluid channels and the chamber, thereby allowing fluid communication between the fluid channels through the chamber (as shown in FIG. 7(b)). The contact and compression between the piston motion control member and the piston 2030 can be adjusted by regulating the movement distance of the manipulation rod. At the same time, the chamber wall 2010 can be configured as a limit for the piston motion control member. In addition, the torque threshold value of the electric screwdriver 3020 is configured so that when the piston motion control member moves to the limit and the manipulation rod in the piston motion control member is subjected to a torque exceeding the stopping torque value set by the electric screwdriver, the electric screwdriver will stop the rotation of the motor, and thus the manipulation rod can be pulled out. In the present invention, a plurality of piston mechanisms can be controlled by a manipulation rod and a manipulation rod motion mechanism, wherein the manipulation rod can, after being removed from a piston mechanism, move to a position corresponding to another piston mechanism.

FIG. 7(b) schematically shows the piston motion control member is controlled to move upward. As shown in FIG. 7(b), when the manipulation rod is inserted into the cavity, the counterclockwise rotation of the manipulation rod can drive the piston motion control member 2050 to rotate along the threads and move upward in the chamber 2020. When the pressure on the piston disappears (e.g., when the piston motion control member is not in contact with the piston), the piston support 2032 returns to its natural state (i.e., the initial state of the piston support 2032 without additional pressure on the piston), in which state the area where the piston support is in contact with the bottom portion of the piston does not cover any one of the openings 2040 connecting the fluid channels and the chamber, thereby allowing fluid communication between the fluid channels through the chamber. When the piston motion control member moves to a top position, the torque is increased due to the limit. When the torque exceeds the stopping torque value set by the electric screwdriver, the electric screwdriver will stop the rotation of the manipulation rod, and thus the manipulation rod can be pulled out.

Figure 8:
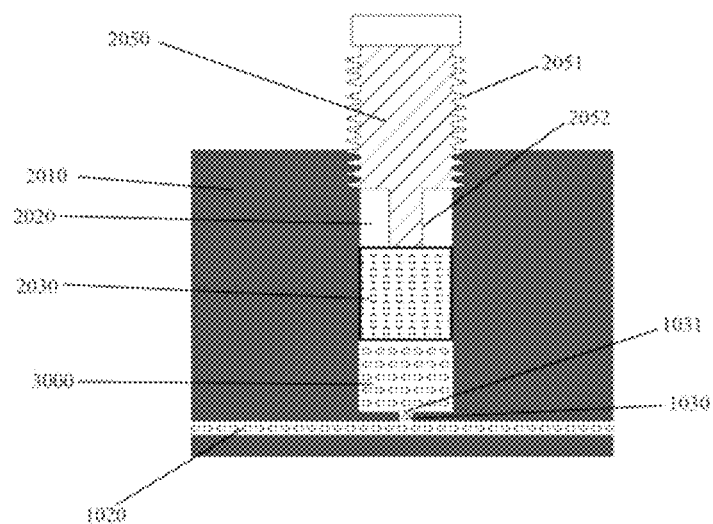
FIG. 8 shows sectional views of another exemplary fluid control device and a piston mechanism employed therein according to the present invention.

FIG. 8 is a sectional view of another exemplary fluid control device according to the present invention, and a piston mechanism employed therein. As shown in FIG. 8, the piston mechanism 2000 comprises a chamber wall 2010, a chamber 2020 formed by a space defined by the chamber wall, a piston 2030 movable within the chamber, and a piston motion control member 2050 for controlling the movement of the piston. A bottom portion of the chamber of the piston mechanism is in communication with a branch channel 1030 of a fluid channel 1020, and an opening 1031 connecting the branch channel 1030 and the chamber is arranged at the bottom portion of the chamber. The piston can move to the bottom portion of the chamber to cover the opening, thereby blocking the communication between the chamber and the fluid channel. In the piston mechanism shown in FIG. 7, the piston motion control member 2050 is provided with external threads 2051, forming a screw thread pair with internal threads of the chamber wall 2010. When rotating along the threads, the piston motion control member 2050 moves upward or downward within the chamber 2020. A lower end portion of the piston motion control member is provided with a piston rod 2052 connected to the piston 2030. When the piston motion control member 2050 rotates along the threads to move upward or downward in the chamber 2020, the piston rod drives the piston to move in the chamber in the same manner.

FIG. 9 shows section views of another exemplary fluid control device according to the present invention, and a piston mechanism employed therein. As shown in FIG. 9, the piston mechanism 2000 comprises a chamber wall 2010, a chamber 2020 formed by a space defined by the chamber wall, a piston 2030 movable within the chamber, and a manipulation rod 3100 for controlling the movement of the piston. A bottom portion of the manipulation rod is provided with a spherical bulge 3120. A bottom portion of the chamber of the piston mechanism is in communication with a branch channel 1030 of a fluid channel 1020, and the opening 1031 connecting the branch 1030 and the chamber is arranged at the bottom portion of the chamber. The piston can move to the bottom portion of the chamber to cover the opening, thus blocking the communication between the chamber and the fluid channel. The piston 2030 is provided with a notch 2031 engageable with the spherical bulge 2053. The manipulation rod is movably connected to the piston by inserting the spherical bulge 3120 at the bottom portion of the manipulation rod into the notch 2031 at the top portion of the piston 2030. The manipulation rod can be rotated or moved upward and downward. A mechanism for controlling the movement of the manipulation rod comprises a member controlling the upward and downward movement as well as the rotation of the manipulation rod, for example, a motor for controlling the manipulation rod to rotate as shown in the drawing. In the present invention, the manipulation rod motion motor may be an electric screwdriver 3130, which can set parameters of the manipulation rod such as rotation direction, rotation speed, rotation angle, stopping torque, etc. FIG. 9(a) schematically shows the piston is controlled to move downward. The manipulation rod, after being inserted into the notch 2031 at the top portion of the piston 2030, moves downward to drive the piston to move in the same manner. In one aspect of the present invention, the manipulation rod can be inserted into the notch at the top portion of the piston in a slowly rotating manner, effectively solving the alignment problem. FIG. 9(b) schematically shows the piston is controlled to move upward. As shown in FIG. 9(b), the manipulation rod, after being inserted into the notch 2031 at the top portion of the piston 2030, moves upward to drive the piston to move in the same manner.

As shown in FIGS. 8 and 9, the fluid in the fluid channel 1020 can be drawn into the chamber as the piston 2030 rises and leaves the bottom portion of the chamber. Fluid can be drawn, released, or retained from or in the chamber, as well as the speed at which the fluid enters or leaves the chamber, can be precisely controlled through the direction of movement, position, and speed of the piston motion control member 2050. As a result, the fluid control device can be applied to the micro or small fluid channel systems, such as microfluidic devices or kits, meeting the need for a certain fluid retained (stored) in a certain area within the system, or discharged therefrom to participate in a reaction.

The aforementioned fluid control device and/or the piston mechanism employed therein disclosed in the second embodiment may be used in micro or small fluid channel systems such as microfluidic devices or kits, which can more effectively control the movement of fluid between chambers, including more accurately controlling the amount of fluid stored in the chamber, the speed of fluid movement in the fluid channel, the communication or closure between the fluid channels, etc.

The fluid control device and/or the piston mechanism employed therein disclosed in the second embodiment may be used for the fluid control device shown in the first embodiment, and to replace the fluid control device shown in the first embodiment or at least one piston mechanism or piston valve mechanism arranged therein. For example, the fluid control device disclosed in the first embodiment comprises at least one first piston mechanism and at least one second piston mechanism, wherein the first piston mechanism and the second piston mechanism comprise a first chamber and a second chamber, respectively, in communication with fluid channels. The first chamber and the second chamber comprise a first piston and a second piston, respectively, wherein the first piston makes a first movement relative to the first chamber and the second piston makes a second movement relative to the second chamber. Due to the first and second movements, the first and the second pistons cause the same volume change in the first and second chambers, but with opposite effects. One or more of at least one first piston mechanism and at least one second piston mechanism is the fluid control mechanism disclosed in the second embodiment, i.e., the bottom portion of the first chamber or the second chamber is in communication with at least one fluid channel, wherein the opening connecting the fluid channel to the chamber is arranged at the bottom portion of the chamber, and the first piston or second piston can move to the bottom portion of the chamber to cover the opening, thereby blocking the communication between the chamber and the fluid channel. For another example, a piston valve mechanism is provided between one or both of the first piston mechanism and the second piston mechanism and the fluid channels in the fluid control device disclosed in the first embodiment, wherein the piston valve mechanism comprises a valve chamber in communication with the fluid channels and a valve piston arranged in the valve chamber. One or more of the piston valve mechanisms may be the fluid control mechanism as previously disclosed, or the piston mechanism arranged therein. That is, the bottom portion of the valve chamber is in communication with at least one fluid channel, wherein the opening connecting the fluid channel and the valve chamber is arranged at a bottom portion of the valve chamber, and the valve piston can move to the bottom portion of the valve chamber to cover the opening, thereby blocking the communication between the valve chamber and the fluid channel.

The foregoing description is merely illustrative of preferred embodiments of the present invention and is not intended to limit the present invention. Any modifications, equivalent substitutions, improvements, and the like within the spirit and principles of the present invention are intended to be included within the scope of protection of the present invention.

The invention claimed is:

1. A fluid control mechanism, comprising:
a chamber, a chamber wall, and a piston and a piston motion control member provided within the chamber,
wherein the piston motion control member is provided with external threads forming a screw thread pair with internal threads on the chamber wall, and is configured to rotate along the internal threads to move within the chamber for driving the piston to move in the chamber; and
at least one fluid channel,
wherein the chamber is configured to be in communication with the fluid channel,
wherein an opening connecting the fluid channel and the chamber is arranged in the chamber, and the piston is configured to be movable in the chamber to cover the opening, thereby blocking communication between the chamber and the fluid channel,
wherein a bottom portion of the piston is provided with a piston support, which is configured as a bulge,
wherein a part of the piston in contact with the bottom portion of the chamber is configured not to cover the opening connecting the fluid channel and the chamber when the piston support is in its natural state; and
the bulge is configured to be flattened due to deformation under pressure, so that the bottom portion of the piston is entirely in complete contact with the bottom portion of the chamber to cover the opening connecting the fluid channel with the chamber, thereby blocking the communication between the chamber and the fluid channel.

2. The fluid control mechanism according to claim 1, wherein the opening connecting the fluid channel and the chamber is arranged at a bottom portion of the chamber, and the piston is configured to be movable to the bottom portion of the chamber to cover the opening, blocking the communication between the chamber and the fluid channel.

3. The fluid control mechanism according to claim 2, wherein a lower end portion of the piston motion control member is provided with a piston rod, which is in contact with the piston at a part configured to be slidably connected to the piston;
the piston motion control member is configured to, when rotating along the internal threads to move in the chamber, drive the piston to move in the chamber; and
the rotation of the piston rod does not drive the piston to rotate substantially.

4. The fluid control mechanism according to claim 3, wherein a bottom portion of the piston rod is provided with a bulge, and a top portion of the piston is provided with a notch engageable with the bulge,
wherein the piston rod is slidably connected to the piston by inserting the bulge into the notch at the top portion of the piston, the rotation of the bulge not driving the piston to rotate substantially, and the piston rod is configured to drive the piston to move upward and downward in the chamber through the same movement of the piston rod.

5. The fluid control mechanism according to claim 1, wherein a cross section of the piston has a diameter of about 0.5-25 mm.

6. The fluid control mechanism according to claim 1, wherein a cross section of the piston has a diameter of about 1-20 mm.

7. The fluid control mechanism according to claim 1, wherein a cross section of the piston has a diameter of about 3-15 mm.

8. The fluid control mechanism according to claim 1, wherein the fluid control mechanism further comprises a manipulation mechanism for controlling movement of the piston motion control member, wherein the manipulation mechanism is configured to be separable from the piston motion control member.

9. The fluid control mechanism according to claim 8, wherein the manipulation mechanism comprises a manipulation rod and a manipulation rod motion mechanism, wherein, the piston motion control member is provided with a cavity suitable for receiving the manipulation rod; and the manipulation rod is configured to fit with the cavity of the piston motion control member after being inserted therein and drive the piston motion control member to rotate when rotating.

10. The fluid control mechanism according to claim 9, wherein the manipulation rod motion mechanism comprises a component for controlling upward and downward movement and rotation of the manipulation rod.

11. The fluid control mechanism according to claim 10, wherein the component is a motor for controlling the rotation of the manipulation rod.

12. The fluid control mechanism according to claim 11, wherein the motor is an electric screwdriver for setting parameters of the manipulation rod, wherein the parameters include at least one of rotation direction, rotation speed, rotation angle, and stopping torque.

13. A fluid control device, comprising:
a housing, a sample inlet, and
a fluid control mechanism, comprising:
a chamber and a chamber wall, as well as a piston and a piston motion control member provided within the chamber,
wherein the piston motion control member is provided with external threads forming a screw thread pair with internal threads on the chamber wall, and is configured to rotate along the internal threads to move within the chamber for driving the piston to move in the chamber; and
at least one fluid channel,
wherein a bottom portion of the chamber is configured to be in communication with the fluid channel,
wherein an opening connecting the fluid channel and the chamber is arranged at the bottom portion of the chamber, and the piston is configured to be movable to the bottom portion of the chamber to cover the opening, thereby blocking communication between the chamber and the fluid channel,
wherein a bottom portion of the piston is provided with a piston support, which is configured as a bulge,
wherein a part of the piston in contact with the bottom portion of the chamber is configured not to cover the opening connecting the fluid channel and the chamber when the piston support is in its natural state; and
the bulge is configured to be flattened due to deformation under pressure, so that the bottom portion of the piston is entirely in complete contact with the bottom portion of the chamber to cover the opening connecting the fluid channel with the chamber, thereby blocking the communication between the chamber and the fluid channel.

* * * * *